(12) United States Patent
Imhoff et al.

(10) Patent No.: US 8,772,445 B2
(45) Date of Patent: Jul. 8, 2014

(54) PRODUCTION AND USE OF ANTITUMORAL CYCLODEPSIPEPTIDES

(75) Inventors: Johannes Imhoff, Preetz (DE); Zhiguo Yu, Shenyang (CN); Gerhard Lang, Gurwolf (CH); Jutta Wiese, Eutin (DE); Holger Kalthoff, Kiel (DE); Stefanie Klose, Wolfsburg (DE)

(73) Assignee: Helmholtz-Zentrum Fuer Ozeanforschung Kiel (Geomar), Kiel (DE)

( * ) Notice: Subject to any disclaimer, the term of this patent is extended or adjusted under 35 U.S.C. 154(b) by 1023 days.

(21) Appl. No.: 12/863,319

(22) PCT Filed: Nov. 20, 2008

(86) PCT No.: PCT/DE2008/001915
§ 371 (c)(1),
(2), (4) Date: Nov. 30, 2010

(87) PCT Pub. No.: WO2009/089810
PCT Pub. Date: Jul. 23, 2009

(65) Prior Publication Data
US 2011/0077205 A1   Mar. 31, 2011

(30) Foreign Application Priority Data

Jan. 18, 2008  (DE) .......................... 10 2008 005 097

(51) Int. Cl.
*C07K 5/00* (2006.01)
*A61K 38/04* (2006.01)

(52) U.S. Cl.
USPC ............ 530/317; 530/330; 514/2.9; 514/19.3

(58) Field of Classification Search
None
See application file for complete search history.

(56) References Cited

U.S. PATENT DOCUMENTS 5,270,334 A   12/1993   O'Sullivan et al.

OTHER PUBLICATIONS

Sabreesh et. al. Identification and Characterization of a Library of Microheterogenous Cyclodepsipeptides from the fungus *Isaria*, The Journal of Natural Products, vol. 70, No. 5 (2007).* http://www.iarc.fr/en/publications/pdfs-online/wcr/2003/WorldCancerReport.pdf , pp. 1-14 of 342 pps.
Worlds Health Statistics—2007, http://www.who.int/whosis/whostat2007_10highlights.pdf.
BC Cancer Agency Cancer Drug Manual—1994, http://www.bccancer.bc.ca/NR/rdonlyres/852A1FC3-5BD2-481B-BFAA-45ACBFA77FAC/22684/Dactinomycinmonograph_5APR07.pdf.
Romero, F. et al., "Thiocoraline, a New Depsipeptide with Antitumor Activity Produced by a Marine Micromonospora. I. Taxonomy, Fermentation, Isolation, and Biological Activities", J. Antibiot. 1997; 50(9): 734-7.
Tan, R.X., "Isolation and Structure Assignments of Rostratins A-D, Cytotoxic Disulfides Produced by the Marine-Derived Fungus *Exserohilum rostratum*.", J. Nat. Prod, Aug. 2004; 67(8): 1374-82.
Wickerham, L.J., "Taxonomy of yeasts", US Dept. Technol. Bull, 1951; 1029: 1-56.
Siegmund, D. et al., "Death receptor-induced signalling pathways are differentially regulated by gamma interferon upstream of caspase 8 processing", Mol. Cell. Biol. 2005; 25: 6363-6379.

* cited by examiner

*Primary Examiner* — James H Alstrum Acevedo
*Assistant Examiner* — Jeanette Lieb
(74) *Attorney, Agent, or Firm* — Diederiks & Whitelaw, PLC

(57) ABSTRACT

A compound having the general structure

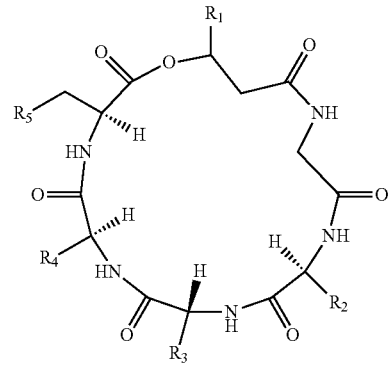

$R_1$, $R_2$, $R_3$ and $R_4$ being selected from the group consisting of a hydrogen atom (H) and a $C_1$-$C_{20}$ alkyl,
and
$R_5$ being a phenyl radical.

9 Claims, No Drawings

PRODUCTION AND USE OF ANTITUMORAL CYCLODEPSIPEPTIDES

CROSS-REFERENCE TO RELATED APPLICATIONS

This application represents a National Stage application of PCT/DE2008/001915 entitled "Production and Use of Antitumoral Cyclodepsipeptides" filed Nov. 20, 2008, pending.

BACKGROUND OF THE INVENTION

The invention relates to cyclical peptides that are suited for producing pharmaceuticals for treating cancer. The invention also relates to a method for producing theses compounds and their use as pharmaceuticals.

Until now many cancers cannot be treated by selectively acting biological agents. According to the World Health Organization (WHO) about 10 million people were diagnosed as having cancer in 2000, about 6 million died (World Cancer Report 2003. http://www.iarc.fr/en/publications/pdfs-online/wcr/2003/WorldCancerReport.pdf). According to WHO estimates the number of deaths caused by cancer will rise to about 11.5 million a year by 2030 (Worlds Health Statistics—2007. http://www.who.int/whosis/whostat2007_10highlights.pdf). Starting approximately from 2010, cancer will be the main cause for deaths after infectious diseases, followed by ischemic cardiac diseases, apoplexy (stroke), and HIV/AIDS.

Peptides produced by microorganisms are among promising candidates for treating cancer. For example actinomycin D that is produced by *Streptomyces parvulus* is already being used a pharamaceutical for treating cancer (BC Cancer Agency Cancer Drug Manual-1994. http://www.bccancer.b-c.ca/NR/rdonlyres/852A1FC3-5BD2-481B-BFAA-45ACBFA77FAC/22684/Dactinomycinmonograph_5APR07.pdf). Thiocoralin, a product of *Micromonspora marina*, inhibits the growth of tumor cells (Romero, F. et al. "Thiocoraline, a New Depsipeptide with Antitumor Activity Produced by a Marine *Micromonospora*. I. Taxonomy, Fermentation, Isolation, and Biological Activities." J. Antibiot. 1997; 50 (9): 734-7). The marine fungus isolate *Exserohilum rostratum* produces the cyclical dipeptides rostratin A-D that are having a cytotoxic effect (Tan, R. X. "Isolation and Structure Assignments of Rostratins A-D, Cytotoxic Disulfides Produced by the Marine-Derived Fungus *Exserohilum rostratum*." J. Nat. Prod. 2004 August; 67(8): 1374-82).

Despite the wide knowledge on the species *Scopulariopsis* even in the marine habitat there is only limited knowledge on natural products from these organisms. As far as we know the only natural product known to date from this species is a pyranol derivate, patented for its antimycotic activity (U.S. Pat. No. 5,270,334).

With a view to the large number of humans that are suffering from cancer, the unfavorable prognosis for curing certain types of cancer (e.g. pancreas) due to the low efficiency of previous pharmaceuticals, side effects, and the development of resistance against pharmaceuticals used there is an urgent need for new cancer pharmaceuticals.

SUMMARY OF THE INVENTION

Therefore the present invention is based on the objective of providing further antitumorally acting peptides and to illustrate a way for their production.

According to the invention, this objective is achieved by a compound having the specified features.

More specifically, according to the invention, this objective is achieved by:
a) a compound having the general structure

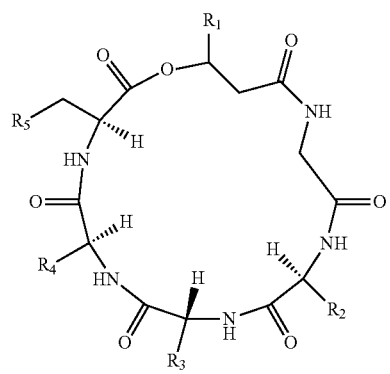

$R_1$, $R_2$, $R_3$ and $R_4$ being selected from the group consisting of a hydrogen atom (H) and a $C_1$-$C_{20}$ alkyl, and $R_5$ being a phenyl radical;
b) a method for producing a compound having the general structure

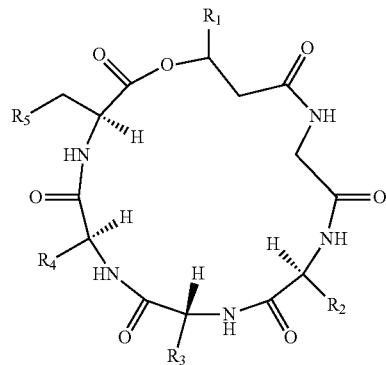

$R_1$, $R_2$, $R_3$ and $R_4$ being selected from the group consisting of a hydrogen atom (H) and a $C_1$-$C_{20}$ alkyl, and $R_5$ being a phenyl radical, characterized by the following steps:
 cultivating a fungus of the species *Scopulariopsis* in a manner known per se and
 isolating the compound from the culture medium and/or the fungus; and
c) the use of a substance having the general structure

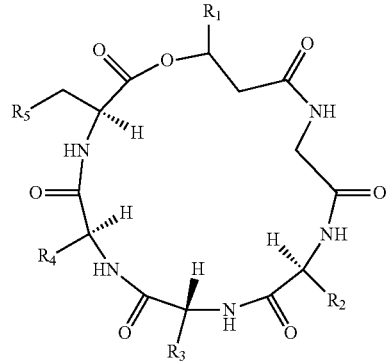

$R_1$, $R_2$, $R_3$ and $R_4$ being selected from the group consisting of a hydrogen atom (H) and a $C_1$-$C_{20}$ alkyl, and $R_5$ being a phenyl radical by: administering the substance as an antitumor agent, such as for the treatment and prophylaxis of pancreatic cancer.

DETAILED DESCRIPTION OF THE INVENTION

During the course of a scientific program for isolating biologically active natural products from marine microorganisms the inventors have examined the fungus *Scopulariopsis brevicaulis*, isolated from the marine sponge *Tethya aurantium*.

The antitumoral peptides Scopularid A and Scopularid B preferred according to the invention were isolated from cultures of the fungus *Scopulariopsis brevicaulis* by preparative HPLC.

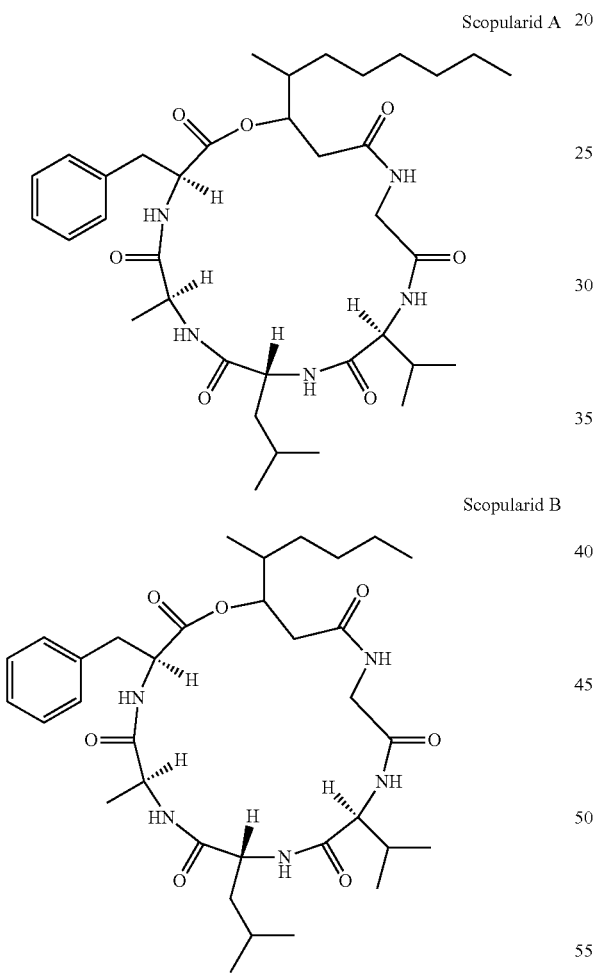

Scopularid A

Scopularid B

The physical data of Scopularid A and B are given in the Tables 1 and 2 that are attached, Table 1 showing the NMR data (600 MHz, MeOD) of Scopularid A and Table showing 2 the NMR data (600 MHz, MeOD) of Scopularid B.

The examination of the antiproliferative effect against tumor cells confirmed that Scopularid B shows a significant inhibitive effect against tumor cell lines, in particular against pancreas tumor cell line Colo357 (cf. Example 4).

The propagation and identification of the fungus *Scopulariopsis brevicaulis* and the purification of Scopularid A and Scopularid B from cultures of the fungus and the determination of the antiproliferative effect against tumor cells are described in the following examples.

1) Propagation of a Culture of the Fungus *Scopulariopsis brevicaulis*

The propagation of the fungus cultures for obtaining Scopularides took place in 2 Liter Erlenmeyer flasks that were each loaded with 700 mL nutrient solution having the following composition (modified according to Wickerham, L. J. "Taxonomy of yeasts." US Dept. Technol. Bull. 1951; 1029: 1-56.): 3.0 g yeast extract; 3.0 g malt extract; 5.0 g peptone; 10.0 g glucose; 30.0 g NaCl; pH 6.8. Sterilization of the nutrient solution was by autoclaving at 121° C./1 bar for 20 minutes. As inoculum for the experimental fungus culture, cell material was transferred from a 14 day old preculture that had been propagated on WM medium into the feed stock of the main culture using an inoculation loop. Incubation of the inoculated nutrition solution was carried out over a period of 14 days at a constant temperature of 28° C. in a static culture in darkness.

2) Identification of the Fungus as *Scopulariopsis brevicaulis*

The morphological features of the fungus are determined using scanning electron microscope examinations. The fungus shows single conidiophores that emerge from hyphae. The hyphae are unbranched or subdivided vertically once or twice. The conidiogenous cells are cylindrical, sometimes with a swollen base, and with an annelating zone of variable length and uniform width. The conidiae are spherical to oval (4-6×6-7 µm) and exhibit a flattened base and rough elevations. Genetic identification is via 18S rDNA analysis. The morphological characteristics and the 18S rDNA sequence result in an unambiguous identification of the fungus as *Scopulariopsis brevicaulis*.

3) Purification of Scopularid A and Scopularid B from Cultures of the Fungus *Scopulariopsis brevicaulis*

The fungus mycelium is separated off the culture supernatant, comminuted and extracted using acetone. The acetone extract is evaporated to dryness, and the residue is rinsed sequentially with a methanol water mixture (2:8) and with n-hexane. The remaining residue is subjected to a separation by preparative high-performance liquid chromatography.

Separation column: Phenomenex Luna C18, 21.2×250 mm, 5 µm

Solvent: water+0.1% formic acid and acetonitrile+0.1% formic acid (30:70)

Flow rate: 18 mL/min

The substances Scopularid A and Scopularid B are eluted after 13 and 8 min. After removing the solvents by drying in a vacuum the desired pure substances are obtained as white solids.

4) Determination of the Antiproliferative Effect Against Tumor Cells

The substances Scopularid A and Scopularid B have shown significant inhibitory action against tumor cell lines, in particular pancreatic tumor cell lines Colo357 and Panc89 and also intestinal tumor cell lines HT29 (on average an inhibition between 25-50% at 1 µg/mL). This activity was determined using the crystal violet assay (Siegmund, D. et al. "Death receptor-induced signalling pathways are differentially regulated by gamma interferon upstream of caspase 8 processing." Mol. Cell. Biol. 2005; 25: 6363-6379).

TABLE 1

Scopularid A
Colorless finely-crystalline solid.
Melting point: 229-230° C.
Optical activity: [α]25D −38° (c 0.5, MeOH)
HRESIMS: m/z 672.4331 [M + H]+ (calculated for $C_{36}H_{58}N_5O_7$ 672.4336)
NMR data (600 MHz; in MeOH-d4)

| Position | | $\delta_C$, mult. | $\delta_H$ (J in Hz) | COSY | HMBC |
|---|---|---|---|---|---|
| Phe | 1 | 173.6, qC | | | |
| | 2 | 55.3, CH | 4.79, m | 3a, 3b | 1, 3 |
| | 3 | 39.4, $CH_2$ | 3.18, dd (13.5, 7.5) | 2, 3b | 1, 2, 4, 5/9 |
| | | | 3.03, dd (13.5, 8.2) | 2, 3a | 1, 2, 4, 5/9 |
| | 4 | 137.8, qC | | | |
| | 5/9 | 130.3, CH | 7.24, m | 6/8 | 3, 7, 5/9 |
| | 6/8 | 129.6, CH | 7.28, m | 5/9 | 4, 6/8 |
| | 7 | 128.0, CH | 7.21, m | | 5/9 |
| Ala | 1 | 174.1, qC | | | |
| | 2 | 50.3, CH | 4.29, q (7.3) | 3 | 1, 3, Leu-1 |
| | 3 | 17.6, $CH_3$ | 1.27, d (7.3) | 2 | 1, 2 |
| Leu | 1 | 175.1, qC | | | |
| | 2 | 54.7, CH | 4.19, m | 3 | 1, 3, 4 |
| | 3 | 40.3, $CH_2$ | 1.58, m | 2, 4 | 1, 2, 4 |
| | 4 | 26.0, CH | 1.68, m | 3, 5, 6 | 2, 3, 5, 6 |
| | 5 | 23.1, $CH_3$ | 1.00, d (6.6) | 4 | 3, 4, 6 |
| | 6 | 22.3, $CH_3$ | 0.95, d (6.6) | 4 | 3, 4, 5 |
| Val | 1 | 173.4, qC | | | |
| | 2 | 59.9, CH | 4.20, m | 3 | 1, 3, 4, Gly-1 |
| | 3 | 31.0, CH | 2.19, m | 2, 4, 5 | 1, 2, 4, 5 |
| | 4 | 19.0, $CH_3$ | 0.98, d (6.7) | 3 | 2, 3, 5 |
| | 5 | 19.7, $CH_3$ | 0.97, d (6.7) | 3 | 2, 3, 4 |
| Gly | 1 | 171.9, qC | | | |
| | 2 | 44.0, $CH_2$ | 4.24, d (16.8) | | 1, HMDA-1 |
| | | | 3.53, d (16.8) | | 1, HMDA-1 |
| HMDA[a] | 1 | 174.5, qC | | | |
| | 2 | 40.9, $CH_2$ | 2.42, m | 3 | 1, 3, 4 |
| | 3 | 78.6, CH | 4.77, m | 2, 4 | 2, 4, 4-Me |
| | 4 | 39.0, CH | 1.54, m | 3, 4-Me | |
| | 5 | 33.6, $CH_2$ | 1.22, m | | |
| | | | 0.95, m | | |
| | 6 | 30.6, $CH_2$ | 1.30, m | | |
| | 7 | 28.2, $CH_2$ | 1.29, m | | |
| | 8 | 33.0, $CH_2$ | 1.26, m | | |
| | 9 | 23.7, $CH_2$ | 1.31, m | 10 | |
| | 10 | 14.42, $CH_3$ | 0.91, t (7.2) | 9 | 9, 8 |
| | 4-Me | 14.41, $CH_3$ | 0.83, d (6.9) | 4 | 3, 4, 5 |

[a]HMDA: 3-hydroxy-4-methyl decanoic acid

TABLE 2

Scopularid B
White amorphous solid
Optical activity: [α]25D −43° (c 0.5, MeOH)
HRESIMS: m/z 644.4007 [M + H]+ (calculated for $C_{34}H_{54}N_5O_7$ 644.4023)
NMR data (600 MHz; in MeOH-d4)

| Position | | $\delta_C$, mult. | $\delta_H$(JJin Hz) | COSY | HMBC |
|---|---|---|---|---|---|
| Phe | 1 | 173.6, qC | | | |
| | 2 | 55.3, CH | 4.78, m | 3a, 3b | 1, 3 |
| | 3 | 39.4, $CH_2$ | 3.18, dd (13.5, 7.5) | 2, 3b | 1, 2, 4, 5/9 |
| | | | 3.03, dd (13.5, 8.2) | 2, 3a | 1, 2, 4, 5/9 |
| | 4 | 137.8, qC | | | |
| | 5/9 | 130.3, CH | 7.24, m | 6/8 | 3, 7, 5/9 |
| | 6/8 | 129.6, CH | 7.28, m | 5/9 | 4, 6/8 |
| | 7 | 128.0, CH | 7.21, m | | 5/9 |
| Ala | 1 | 174.1, qC | | | |
| | 2 | 50.3, CH | 4.29, q (7.3) | 3 | 1, 3, Leu-1 |
| | 3 | 17.6, $CH_3$ | 1.28, d (7.3) | 2 | 1, 2 |
| Leu | 1 | 175.1, qC | | | |
| | 2 | 54.7, CH | 4.19, m | 3 | 1, 3, 4 |
| | 3 | 40.4, $CH_2$ | 1.58, m | 2, 4 | 1, 2, 4 |
| | 4 | 26.0, CH | 1.69, m | 3, 5, 6 | 2, 3, 5, 6 |
| | 5 | 23.1, $CH_3$ | 0.99, d (6.6) | 4 | 3, 4, 6 |
| | 6 | 22.3, $CH_3$ | 0.95, d (6.6) | 4 | 3, 4, 5 |

TABLE 2-continued

Scopularid B
White amorphous solid
Optical activity: [α]25D −43° (c 0.5, MeOH)
HRESIMS: m/z 644.4007 [M + H]+ (calculated for $C_{34}H_{54}N_5O_7$ 644.4023)
NMR data (600 MHz; in MeOH-d4)

| Position | | $\delta_C$, mult. | $\delta_H$(J Jin Hz) | COSY | HMBC |
|---|---|---|---|---|---|
| Val | 1 | 173.4, qC | | | |
| | 2 | 59.9, CH | 4.20, m | 3 | 1, 3, 4, Gly-1 |
| | 3 | 31.0, CH | 2.18, m | 2, 4, 5 | 1, 2, 4, 5 |
| | 4 | 19.0, $CH_3$ | 0.98, d (6.7) | 3 | 2, 3, 5 |
| | 5 | 19.7, $CH_3$ | 0.97, d (6.7) | 3 | 2, 3, 4 |
| Gly | 1 | 171.9, qC | | | |
| | 2 | 44.0, $CH_2$ | 4.24, d (16.8) | | 1, HMOA-1 |
| | | | 3.53, d (16.8) | | 1, HMOA-1 |
| $HMOA^a$ | 1 | 174.5, qC | | | |
| | 2 | 40.9, $CH_2$ | 2.41, m | 3 | 1, 3, 4 |
| | 3 | 78.6, CH | 4.77, m | 2, 4 | 2, 4, 4-Me |
| | 4 | 39.0, CH | 1.54, m | 3, 4-Me | |
| | 5 | 33.3, $CH_2$ | 1.22, m | | |
| | | | 0.96, m | | |
| | 6 | 30.5, $CH_2$ | 1.32, m | 6b | |
| | | | 1.32, m | 6a | |
| | 7 | 23.8, $CH_2$ | 1.16, m | 8 | |
| | 8 | 14.38, $CH_3$ | 0.90, t (7.2) | 7 | 6, 7 |
| | 4-Me | 14.41, $CH_3$ | 0.83, d (6.9) | 4 | 3, 4, 5 |

$^a$HMOA: 3-hydroxy-4-methyl octane acid

Based on the above, it should be readily apparent that the objects of the invention are achieved by:

a) a compound having the general structure

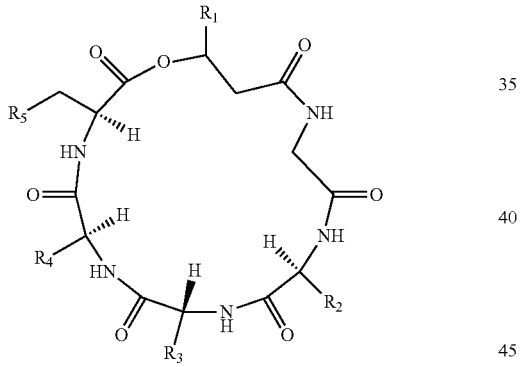

$R_1$, $R_2$, $R_3$ and $R_4$ being selected from the group consisting of a hydrogen atom (H) and a $C_1$-$C_{20}$ alkyl, and $R_5$ being a phenyl radical;

b) a method for producing a compound having the general structure

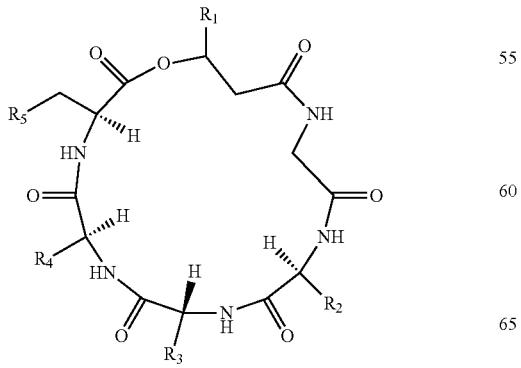

$R_1$, $R_2$, $R_3$ and $R_4$ being selected from the group consisting of a hydrogen atom (H) and a $C_1$-$C_{20}$ alkyl, and $R_5$ being a phenyl radical, characterized by the following steps:
cultivating a fungus of the species *Scopulariopsis* in a manner known per se and
isolating the compound from the culture medium and/or the fungus; and c) the use of a substance having the general structure

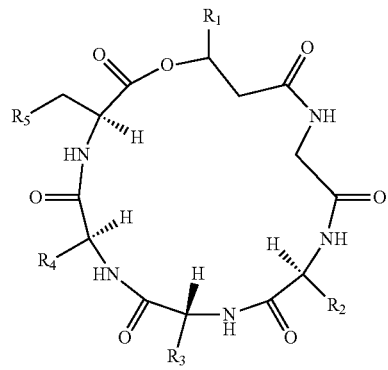

$R_1$, $R_2$, $R_3$ and $R_4$ being selected from the group consisting of a hydrogen atom (H) and a $C_1$-$C_{20}$ alkyl, and $R_5$ being a phenyl radical by: administering the substance as an antitumor agent, such as for the treatment and prophylaxis of pancreatic cancer.

In particular forms, the substance or compound is characterized in that at least one of $R_1$-$R_4$ is a $C_1$-$C_{20}$ alkyl, or $R_5$ is a phenyl, having a substituent selected from the group consisting of an acyl radical, a formyl, acetyl, trichloroacetyl, fumaryl, maleyl, succinyl, or benzoyl group, a halogen radical, an aminoalkyl group, a hydroxyl group, an ether group or a carboxyl group the compound having the general structure.

The invention claimed is:

1. A compound having the general structure

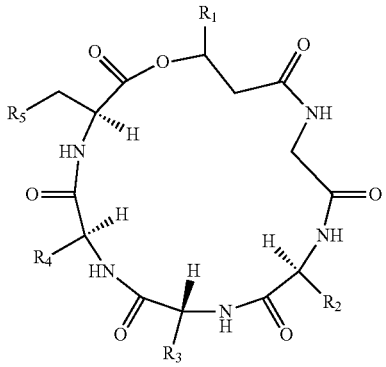

$R_1$, $R_2$, $R_3$ and $R_4$ being selected from the group consisting of a hydrogen atom (H) and a $C_1$-$C_{20}$ alkyl, and $R_5$ being a phenyl radical.

2. The compound according to claim 1, characterized in that at least one of $R_1$, $R_2$, $R_3$ and $R_4$ is a $C_1$-$C_{20}$ alkyl having a substituent selected from the group consisting of an acyl radical, a formyl, acetyl, trichloroacetyl, fumaryl, maleyl, succinyl, or benzoyl group, a halogen radical, an aminoalkyl group, a hydroxyl group, an ether group or a carboxyl group.

3. The compound according to claim 1 having the following formula (Scopularid A)

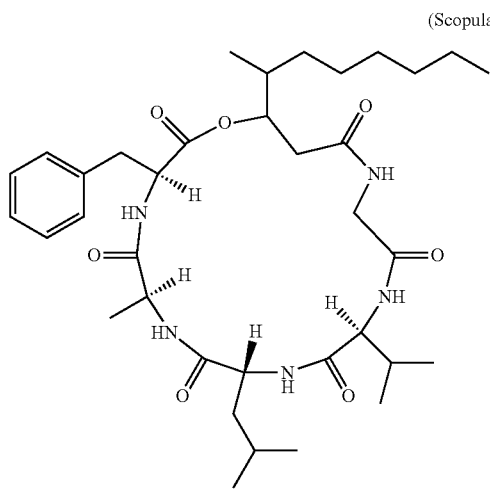

including its diastereomeres.

4. The compound according to claim 1 having the following formula (Scopularid B)

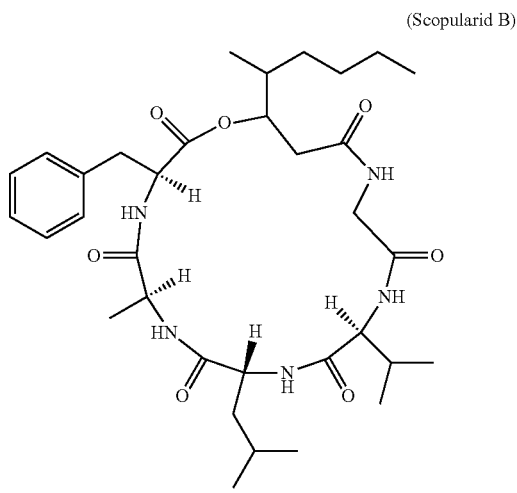 [SMILES: CCCCC(C)C1CC(=O)NCC(=O)N[C@@H](C(C)C)C(=O)N[C@H](CC(C)C)C(=O)N[C@@H](C)C(=O)N[C@@H](Cc2ccccc2)C(=O)O1]

including its diastereomeres.

5. A method for producing a compound having the general structure

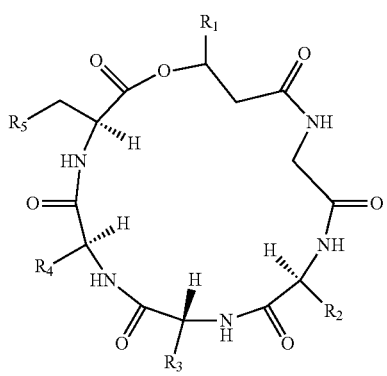

$R_1$, $R_2$, $R_3$ and $R_4$ being selected from the group consisting of a hydrogen atom (H) and a $C_1$-$C_{20}$ alkyl, and $R_5$ being a phenyl radical characterized by the following steps:

a. cultivating a fungus of the species *Scopulariopsis* and b. isolating the compound from the culture medium and/or the fungus.

6. The method according to claim 5, characterized in that the fungus is *Scopulariopsis brevicaulis*.

7. A method of treating pancreatic or intestinal cancer by administering a substance having the general structure

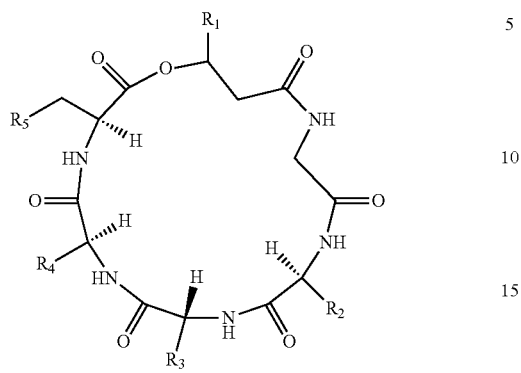

$R_1$, $R_2$, $R_3$ and $R_4$ being selected from the group consisting of a hydrogen atom (H) and a $C_1$-$C_{20}$ alkyl,
and
$R_5$ being a phenyl radical
as an antitumor agent.

8. The method of claim 7 wherein the substance is administered for the treatment of pancreatic cancer.

9. The compound according to claim 1, characterized in that $R_5$ is a phenyl radical having a substituent selected from the group consisting of an acyl radical, a formyl, acetyl, trichloroacetyl, fumaryl, maleyl, succinyl, or benzoyl group, a halogen radical, an aminoalkyl group, a hydroxyl group, an ether group or a carboxyl group.

* * * * *